United States Patent [19]

Alkire et al.

[11] Patent Number: 5,607,697
[45] Date of Patent: Mar. 4, 1997

[54] TASTE MASKING MICROPARTICLES FOR ORAL DOSAGE FORMS

[75] Inventors: Todd G. Alkire, Crystal; Ronald A. Sanftleben; Steven S. Schuehle, both of Maple Grove, all of Minn.

[73] Assignee: Cima Labs, Incorporated, Eden Prairie, Minn.

[21] Appl. No.: 478,419

[22] Filed: Jun. 7, 1995

[51] Int. Cl.⁶ .................... A61K 9/18; A61K 9/20; A61K 9/46
[52] U.S. Cl. .................. 424/495; 424/490; 424/464; 424/466; 514/974
[58] Field of Search ........................ 424/494, 495, 424/497, 490, 464, 466

[56] References Cited

U.S. PATENT DOCUMENTS

| | | | |
|---|---|---|---|
| 4,590,075 | 5/1986 | Wei et al. | 426/5 |
| 4,824,681 | 4/1989 | Schobel et al. | 426/5 |
| 4,994,260 | 2/1991 | Kallstrand et al. | 424/10 |
| 5,126,151 | 6/1992 | Bodor et al. | 426/99 |
| 5,178,878 | 1/1993 | Wehling et al. | 424/466 |

FOREIGN PATENT DOCUMENTS

| | | |
|---|---|---|
| 2032211 | 6/1991 | Canada . |
| 0272220 | 12/1987 | European Pat. Off. . |
| 92/11084 | 7/1992 | WIPO . |

*Primary Examiner*—Thurman K. Page
*Assistant Examiner*—James M. Spear
*Attorney, Agent, or Firm*—Lerner, David, Littenberg, Krumholz & Mentlik

[57] ABSTRACT

The present invention relates to a solid dosage form including a new type of taste masking microparticle having an adsorbate of, for example, mannitol, in the core thereof.

17 Claims, No Drawings

TASTE MASKING MICROPARTICLES FOR ORAL DOSAGE FORMS

FIELD OF THE INVENTION

The present application relates to the field of orally ingested solid dosage forms.

BACKGROUND OF THE INVENTION

A constant problem in the treatment of patients is their inability or unwillingness to swallow solid dosage forms such as tablets. This problem is most frequently encountered in children and the elderly. The problem is, however, not uncommon in healthy adults as well. Although this problem may seem innocuous or idiosyncratic, the fact remains that the inability or unwillingness of some people to take certain dosage forms can severely compromise the patient's compliance with a prescribed treatment protocol. Moreover, due to embarrassment, many patients are unwilling to tell their doctor of their problem so that the doctor can consider other drugs and/or alternate vehicles. Of course, such a lack of compliance can delay treatment or cure.

To overcome these problems, the pharmaceutical industry has developed syrups, elixirs, microcapsule containing slurries and unique tablets which dissolve in liquid prior to being consumed. Unfortunately, each of these dosage forms has its own limitations. Often, such dosage forms are more costly than traditional solid dosage forms such as simple tablets or capsules, both in terms of production, but also packaging.

From the consumer's side, alternate dosage forms also have significant disadvantages in terms of convenience. For example, effervescent tablets which are intended to be dissolved in a glass of liquid require the provision of a glass of liquid and a waiting period sufficient to allow the tablet to completely dissolve. Often, these dosage forms leave an objectionable scum which must be wiped out of the glass. Syrups and other liquid are often difficult or inconvenient to carry and inconvenient to take.

This problem is of course not limited to human patients. Animals are often no more willing to take pills than their human counterparts. Of course, it may be possible to mix tablets with an animal's food. However, certain dosage forms may require administration other than at regular feeding times. If a tablet could be devised which would be difficult for an animal to spit out, it might be easier to administer medication thereto.

One particularly innovative solution to these problems was described in Wehling et al., U.S. Pat. No. 5,178,878 which relates to certain effervescent dosage forms including microparticles. The effervescent dosage forms of Wehling et al. provide a significant advance over the art in that they provide an effervescent dosage form for direct oral administration. The dosage form is designed to disintegrate rapidly in the mouth releasing its microparticles as a slurry for ingestion. The dosage forms produced in accordance with Wehling et al. can be placed in the patients mouth and the effervescence contained therein will be activated by contact by the patient's saliva. The tablet will then disintegrate in a number of seconds.

This dosage form is particularly efficacious for administering fragile, rupturable microparticles and, in particular, rapid or immediate release microparticles for dosage forms which will be dosed, for example, every 4–6 hours. "Rapid release" is intended to mean that the microparticles will help mask the objectionable taste of a drug being administered, but once out of the mouth and in the digestive tract, the microparticle will provide as little an impediment as possible to the otherwise normal delivery profile of a drug contained therein. Such microparticles often tend to be broken when chewed. This causes the release of objectionable tasting drugs into the mouth of the patient. However, because the dosage form disintegrates so rapidly, the number of microparticles which can be crushed and thereby, the amount of material which can be released into the mouth is limited such that the sweeteners, flavorings and effervescent sensation of the disintegrating tablet can taste mask the objectionable taste.

Källstrand, et al., U.S. Pat. No. 4,994,260 relates to a pharmaceutical mixture. The mixture is used for the controlled release of a substance. According to Källstrand, et al., a liquid dosage form is produced using either a dry powder or microcapsules which are suspended in a solution of a release-controlling substance, also referred to as a "sink". Alternatively, it is possible to encapsulate the release-controlling substance, together with a drug, within an encapsulating shell. The release-controlling substance may include, inter alia, carbohydrates and carbohydrate-related compounds, disaccharides, monosaccharides, glycerol, glycol, glycosides of monosaccharides and substances derived from ethyleneglycol.

Boder et al., U.S. Pat. No. 5,126,151 relates to an encapsulation mixture. Boder et al. refers to the construction of gums and candies in oral dosage forms. According to Boder et al., microcapsules are produced including a core material which can be selected from a wide variety of materials including sweeteners, medicaments, drugs, flavoring agents and the like. These materials can be used, either singularly or in combination, in either a single or multiple part delivery system. That is, one or more of these materials may be present within one coating matrix or maybe separately coated by the matrix and employed alone or in combination in the final product. The resulting formulations are said to be able to provide a masking of unpleasant tasting drugs such as potassium chloride and the like, making consumption of the drug more appealing to the public. The dosage forms may be prepared in chewable tablet form.

Also of interest may be Schobel et al., U.S. Pat. No. 4,824,681, and Wei et al., U.S. Pat. No. 4,590,075. Encapsulated sweeteners have also been used to provide an extended release of sweetening in, for example, chewing gum, see for example European patent application EPO 87-810747 to Schobel et al. and in bakery products such as disclosed in WO 91-US9434 filed Dec. 17, 1991 to Redding et al.

The present invention provides an improvement over the art by advancing the pioneering technology described in the aforementioned Redding et al. patent.

SUMMARY OF THE INVENTION

In accordance with the present invention there is provided a solid pharmaceutical dosage form adapted for direct oral administration, in solid form, to a mammal. The dosage form includes a plurality of microparticles. Each microparticle has a core which includes at least one pharmaceutical ingredient and a compound which is sweet in taste and which has a negative heat of solution. A binder and/or other excipient may also be disposed within the core. A coating material which will retard dissolution of the pharmaceutical ingredient in the mouth, as well as the objectionable taste of said pharmaceutical ingredient surrounds at least a portion of the core; preferably, the core is completely coated. The solid dosage form is sized, shaped, and compressed to a hardness adapted for direct oral administration. The dosage form is substantially completely disintegratable in the mouth so as to release said microparticles.

Preferred dosage forms according to the present invention include microparticles having a core or center of active ingredients such as drugs, vitamins, dietary supplements, etc. granulated with, mixed with or adsorbed onto, for example, a sugar alditol such as, mannitol. Often this is accomplished using a suitable binder. The core may be spray coated with a coating material, such as, for example, a polymeric film of ethylcellulose and a plasticizer. The resulting microparticles can then be incorporated into one or more types of solid dosage forms. The result is an enhancement in taste masking.

Consider, for example, incorporating microparticles in accordance with the present invention into an effervescent delivery system. While the effervescent tablets will rapidly dissolve in the mouth, with minimal or no chewing, it is possible that they will nonetheless be chewed to some extent. Thus, the coating material used for the microparticle may be compromised and objectionable tasting material may be released into the mouth. The amount of such coating compromised, if any, is far less than that which would occur with a non-effervescent dosage form. Under most circumstances, the amount of material released with the effervescent dosage form is relatively minor; the effervescence and other conventional flavorings contained in the dosage form will be adequate to mask any objectionable taste. However, in unusual situations where significant rapid chewing occurs, where the microparticles are particularly fragile, where the dosage of active ingredient is particularly high and/or where the taste of the active ingredient is particularly objectionable, additional taste masking may be desirable.

Preferred dosage forms in accordance with the present invention achieve this additional measure of protection in several ways. First, the microparticle in accordance with the present invention includes within it a compound which is sweet to the taste and also, preferably, has a negative heat of solution. Compounds falling into this category include, for example, mannitol and sorbitol. Of course, sugars or artificial sweeteners to which, for example, menthol have been added will also work as well. By locating this sweetening compound within the core of individual microparticles, such materials will only play a role in taste masking when needed, i.e., when the coating of the individual microparticle becomes compromised. Therefore, taste masking is provided on an "as needed" basis.

Although the present invention is not limited by any theory of operation, it is believed that this is particularly important because, as the patient begins to swallow, it is possible that some microparticles will remain in the mouth while much of the flavoring and effervescent material will begin its way into the digestive tract. Any microparticles to rupture at that point would have relatively little external taste masking for protection. The formulation of the present invention, however, would provide an additional measure of taste masking at the point where the microparticles are ruptured.

In addition, the present invention makes the design of microparticles and dosage forms much easier. Since the microparticles in accordance with the present invention only participate in taste masking when needed, it is easier to design dosage forms which are not so sweet as to offend the taste of many patients. Some chewable dosage forms use significant sweetening to mask objectionable tastes. However, they may also render the dosage form unpalatable. This in turn enhances the willingness of patients to utilize the dosage form.

The extra level of taste masking protection afforded in accordance with the present invention also allows for the use of microparticles which may be less than perfect. Some or all of the microparticles may include partially coated agglomerates, incompletely coated particles and the like and the patient will still be protected from objectionable taste. In addition, because of the protection afforded by the microparticles of the present invention, less sweetener is required to achieve a given amount of taste masking. Thus, it is possible to design dosage forms which are lower in volume as it is possible to eliminate much of the external sweetener or flavoring used in conventional dosage forms.

The use of microparticles in accordance with the present invention also allows for the design of dosage forms which are non-effervescent. The dosage forms in accordance with Wehling et al. are particularly efficacious at least in part because of the co-action of various taste masking techniques including the use of a microencapsulant around the medicament, conventional flavorings, and the organoleptic sensation resulting from effervescent material. However, in accordance with one embodiment of the present invention, microparticles with sweetened cores can be used in conjunction with other solid, effervescent and non-effervescent dosage forms which dissolve rapidly in the mouth. For example, a freeze dried tablet matrix of sugar may act as a carrier for the microparticles as can table triturate. The dosage forms of the present invention may also include other drugs which have either not been encapsulated or encapsulated using conventional technology.

Further advantages are also obtained by the specific selection of the sweetening agent used in accordance with the present invention. It has been found that the use of certain compounds which are both sweet and have a negative heat of solution provide particular advantages. As previously discussed, the rupture of microparticles in accordance with the present invention may occur when the taste masking capability of the conventional dosage form is greatly reduced. Mannitol and similar compounds provide not only additional sweetness, but also a negative heat of solution which is characterized by a cooling sensation. The combination of sweetness and the cooling sensation provide a level of taste masking not otherwise available given the volume of material involved. In addition, the sweetness and cooling sensation resulting from the use of such compounds can be tailored so as to be complimentary with either the effervescent sensation and/or the conventional flavorings used in the remainder of the dosage form.

DETAILED DESCRIPTION OF THE PREFERRED EMBODIMENTS

"Pharmaceutical ingredients" or "active agents" in accordance with the present invention include systematically distributable pharmaceutical ingredients, vitamins, minerals, dietary supplements, as well as nonsystemically distributable drugs. Pharmaceutical ingredients may include, without limitation, antacids, analgesics, anti-inflammatories, antibiotics, laxatives, anorexics, antihistamines, antiasthmatics, antidiuretics, antiflatuents, antimigraine agents, antispasmodics, sedatives, antihyperactives, antihypertensives, tranquilizers, decongestants, beta blockers and combinations thereof. Also encompassed by the terms "pharmaceutical ingredient(s)" and "active agents" are the drugs and pharmaceutical active ingredients described in Mantelle U.S. Pat. No. 5,234,957 includes 18 through 21. That text is hereby incorporated by reference.

As used in this disclosure, the term vitamin refers to trace organic substances that are required in the diet. For the purposes of the present invention, the term vitamin(s) include, without limitation, thiamine, riboflavin, nicotinic acid, pantothenic acid, pyrdoxine, biotin, folic acid, vitamin $B_{12}$, lipoic acid, ascorbic acid, vitamin A, vitamin D, vitamin E and vitamin K. Also included within the term vitamin are the coenzymes thereof. Coenzymes are specific chemical forms of vitamins. Coenzymes include thiamine pyrophosphates (TPP), flavin mononucleotide (FMM), flavin adenine dinucleotive (FAD), Nicotinamide adenine dinucleotide (NAD), Nicotinamide adenine dinucleotide phosphate (NADP) Coenzyme A (CoA) pyridoxal phosphate, biocytin, tetrahydrofolic acid, coenzyme $B_{12}$, lipoyllysine, 11-cis-retinal, and 1,25-dihydroxycholecalciferol. The term vitamin(s) also includes choline, carnitine, and alpha, beta, and gamma carotenes.

As used in this disclosure, the term "mineral" refers to inorganic substances, metals, and the like required in the human diet. Thus, the term "mineral" as used herein includes, without limitation, calcium, iron, zinc, selenium, copper, iodine, magnesium, phosphorus, chromium and the like, and mixtures thereof.

The term "dietary supplement" as used herein means a substance which has an appreciable nutritional effect when administered in small amounts. Dietary supplements include, without limitation, such ingredients as bee pollen, bran, wheat germ, kelp, cod liver oil, ginseng, and fish oils, amino-acids, proteins and mixtures thereof. As will be appreciated, dietary supplements may incorporate vitamins and minerals.

In general, the amount of pharmaceutical ingredient incorporated in each tablet may be selected according to known principles of pharmacy. An effective amount of pharmaceutical ingredient is specifically contemplated. By the term effective amount, it is understood that, with respect to for example pharmaceuticals, a pharmaceutically effective amount is contemplated. A pharmaceutically effective amount is the amount or quantity of a drug or pharmaceutically active substance which is sufficient to elicit the required or desired therapeutic response, or in other words, the amount which is sufficient to elicit an appreciable biological response when administered to a patient. As used with reference to a vitamin or mineral, the term "effective amount" means an amount at least about 10% of the United States Recommended Daily Allowance ("RDA") of that particular ingredient for a patient. For example, if an intended ingredient is vitamin C, then an effective amount of vitamin C would include an amount of vitamin C sufficient to provide 10% or more of the RDA. Typically, where the tablet includes a mineral or vitamin, it will incorporate higher amounts, preferably about 100% or more of the applicable RDA.

The amount of active agent used can vary widely from a few milligrams to 2500 milligrams or more. Of course, the size of the dosage form, the requirements of other ingredients, and the number of, for example, tablets which constitute a single dose will impact the upper limit on the amount of pharmactive ingredient which can be used. If an active ingredient is particularly nasty tasting and effervescent agents, conventional taste masking agents, and a high amount of mannitol are needed, then the amount of drug that can be delivered will be limited for a given size. Generally, however between about 0.1 and 2,000 milligrams of active agent will be used in accordance with the present invention. More preferably between about 1 and about 500 milligrams and most preferably between about 5 and about 250 milligrams of active agent are used. Stated another way, between about 0.1 and about 67% of the dosage form may be active agent based upon the weight of the finished dosage form. More preferably, the amount of active agent may vary from between about –0.6 and about 34% by weight based on the total weight of the finished dosage form. (A 750 mg tablet was used for this calculation.)

The composition which is sweet in taste and which has a negative heat of solution in accordance with the present invention may include, without limitation, mannitol, sorbitol, xylitol and the like. Other compounds meeting these criteria can be constructed by mixing, for example, sucrose or fructose with flavorings which have a negative heat of solution such as, for example, menthol in methyl salicylate. The result would be a composition which is both sweet and which provides a cooling sensation of compounds having a negative heat of solution. Artificial sweeteners such as saccharin or aspartame may also be used in this fashion.

The amount of sweetening compound used may depend on a number of factors including the size of the resulting microparticles, the size or volume of the resulting tablet, the sturdiness of the microparticle-coated microparticulant, the speed at which the tablet will disintegrate in the mouth, the degree of sweetness imparted by the particular sweetener used, either in the microparticle or in the tablet, or both, the amount of drug used, and the like. For example, particularly rugged microparticles may be less likely to break during chewing and/or compression. Therefore, the amount of material which must be provided to protect against the release of objectionably flavored material may be lessened. If, on the other hand, the active agent is extremely objectionable in taste, then despite the rugged coating, a greater relative amount of sweetening compound may be required. Generally, the amount sweetening material used will range from greater than zero to about 80 percent of the weight of the resulting microparticle.

The sweetener and active agent may be combined in any number of known ways, such as wet granulation, dry granulation, agglomeration, spray coating may be used. For example, the sweetener may be used as an adsorbent for the active agent. Alternatively, particles of each may also be simply mixed together. One or more binders, or other adjuvants may also be used such binders may also be used in the formulation of a tablet as well. Binders include, for example: starch- 5–10% as an aqueous paste; pregelatinized starch- 5–10% added dry to powder; gelatin- 2–10% as an aqueous solution or 2% in starch paste; polyvinylpyrrolidone- 2–20% in an aqueous or alcoholic solution; methylcellulose- 2–10% as an aqueous solution; sodium carboxy methylcellulose- 2–10% as an aqueous solution; ethylcellulose- 5–10% as an alcohol or hydroalcoholic solution; polyacrylamides (Polymer JR)- 2–8% as an aqueous solution; polyvinyloxoazolidone (Devlex)- 5–10% as an aqueous or hydroalcoholic solution; and polyvinyl alcohols- 5–20% in aqueous solutions.

Other adjuvants may also be used in forming the core of the microparticles of the present invention or indeed, in formulating dosage forms as well. Adjuvants include, for example, calcium sulfate NF, Dibasic Calcium phosphate NF, Tribasic calcium sulfate NF, starch, calcium carbonate, microcrystalline cellulose, modified starches, lactose, sucrose and the like, sta-Rx, Avicel, Solka-Floc BW40, Alginic acid, Explotab, AUTOTAB, Guargum, Kaolin, Vecgum, Bentonite, etc. In general, these may be used in up to 20% w/w, but often are used in amounts as low as 3–5% w/w.

The protective coating materials used in accordance with the present invention may include any of the polymers conventionally utilized in the formation of microparticles, matrix-type microparticles and microcapsules. Among these are cellulosic materials such as naturally occurring cellulose and synthetic cellulose derivatives; acrylic polymers and vinyl polymers. Other simple polymers include eproteinaceous materials such as gelatin, polypeptides and natural and synthetic shellacs and waxes. Protective polymers may also include ethylcellulose, methylcellulose, carboxymethyl cellulose and acrylic resin material sold under the registered trademark EUDRAGIT by Rhone Pharma GmbH of Weiterstadt, Germany. Other coating materials include: Gelatin, Gelatin/acacia; Gelatin/acacia/vinylmethylether maleic anhydride; Gelatin/acacia/ethylenemaleic anhydride; carboxymethy-cellulose; Propylhydroxy cellulose; polyvinylalcohol, cellulose acetate phthalate, ethylenevinyl acetate, Nitrocellulose, shellac, and wax.

Generally, it is preferred that the coating will be used in at least about 5 percent based on the weight of the resulting microparticles. More preferable, the coating should constitute at least about 10 percent by weight of the microparticle. The upper limit of protective coating material used is generally less critical, except that where a rapid release of the active ingredient is desire, the amount of coating material should not be so great that the coating material impede the release profile of the active agent or pharmaceutical ingredient when ingested. Thus it may be possible to use greater than 100 percent of the weight of the core thus providing a relatively thick coating. Generally, however, no more than about 75 percent of the weight of the microparticle will be coating material and, more preferably, no more than about 50 percent of the weight of the microparticulate will be coating. Microparticles in accordance with the present invention may range in size. The lower limit of the size is not important so long as taste masking is not compromised, particles should generally not be longer than 1,000 microns and preferably no longer than 850 microns.

Microparticles in accordance with the present invention generally relate to discrete particles containing an active ingredient or pharmaceutical ingredient, at least one compound which is sweet in taste and which has a negative heat of solution and a coating material. Microparticles may be discrete granular material which has been independently and substantially (greater than about 90% of the particles completely coated) coated with a coating material which will retard dissolution of the pharmaceutical ingredient.

This, thereby, prevents direct exposure of the taste buds of the patient to the objectionable tasting predicament. In the context of the present invention, however, the term microparticle also includes crystalline or granular base material which have been imperfectly coated such that some, or all of the particles are not completely coated with the material. Also, useful in accordance with the present invention, and falling within the scope of the term microparticle, are agglomerate matrices whereby an agglomerate is dispersed in a wet coating material which is later broken up, ground or milled. The result may be incompletely coated particle, or particles which are stuck together with the coating material serving as the glue.

In addition to the coating materials just described, various other additives such as, for example, cross linkers, pore-formers, swelling agents, solubility modifiers, plasticizers, and the like may be included within the coating.

In accordance with the present invention, the dosage form may range from between about 50 to about 2,000 milligrams in overall weight. More preferably, the dosage form may range from about 100 to about 1,000 milligrams. The amount of microparticles should make up from about 1 to about 80 percent of that overall weight. More preferably, about 5 to about 50 percent of the dosage forms should be microparticles, by weight.

Ingredients and methods for making microparticles are well-known in the art. Methods of microencapsulation, for example, are described in the aforementioned Lieberman text, *Pharmaceutical Dosage Form: Tablets Volume* 1, Second Edition, New York, 1989, at pages 372–376. The disclosure of Lieherman is hereby incorporated by reference herein. One method taught in Lieberman is the technique of phase separation or coacervation which involves processing three mutually immiscible phases, one containing the pharmaceutical ingredient, another containing the protective coating material and a third containing a liquid vehicle used only in the manufacturing phase. The three phases are mixed and the protective material phase deposits by adsorption on the pharmaceutical ingredient phase. After this step, the protective material phase is converted to a substantially solid form by cross-linking or by removal of solvent from this phase. Other common techniques may be used for forming matrix-type microparticles wherein the pharmaceutical ingredient is dispersed in the protective material. For example, the pharmaceutical ingredient and a solution of a polymeric protective material may be sprayed to form droplets and contacted with a gas such as hot air so as to remove the solvent from the droplets. Such a mixture may also be dried to a solid and then comminuted to form the microparticles. Alternatively, the mixture of the pharmaceutical ingredient and polymeric solution may be mixed with an immiscible liquid phase and the solvent may be removed through this phase. The mixing step may include emulsification of the phase bearing the pharmaceutical ingredient and the protective material in the immiscible liquid phase. Preferably, a spray coating or conservation coating technically may be used.

The microparticles in accordance with the present invention may provide for a timed or sustained release of the pharmaceutical ingredient contained therein. Microparticles may also be provided which are rapid release in nature i.e. where at least 50 percent of the pharmaceutical ingredient is released within approximately one hour or less when tested as described in the examples. The microparticles may also be enteric, i.e., designed to dissolve and release the therapeutic material in the intestines.

In addition to the microparticles in accordance with the present invention, the dosage forms in accordance with the present invention may include flavors, diluents, colors, binders, fillers, compaction vehicles, non-effervescent disintegrants, and lubricants such as those disclosed in Wehling et al. The microencapsulated active ingredients may also be mixed into, for example, a tablet including other active ingredients which are not microencapsulated. The latter, obviously, preferably are not objectionable in taste or can be adequately taste masked by other conventional means. Similarly, the microparticles in accordance with the present invention may also be used with other conventional forms of microparticles in a single dosage form.

Tablet binders may be used in an amount of about 60 weight percent and preferably about 10 percent to 40 percent based on the weight of the total composition. Noneffervescent disintegrant such as, for example, starches, sweeteners, microcrystalline cellulose and the like may also be used and may comprise up to about 20 weight percent, preferably between about two percent and about ten percent of the total weight composition. Coloring agents used may range from between about 0.1 to 3.5 weight percent of the total composition. Flavors incorporated into the composition may be chosen from synthetic flavor oils and flavoring aromatics and/or natural oils, extracts from plants, leaves, flowers, fruits and so forth, and combinations thereof. These may include cinnamon oils, oil of wintergreen, peppermint oils, clover oil, bay oil, anise oil, eucalyptus, vanilla, citrus oil such as lemon oil, orange oil, grape and grapefruit oil, fruit essences including apple, peach, pear, strawberry, raspberry, cherry, plum, pineapple, apricot and so forth. Flavors may be present in the amount of ranging from about 0.5 to 3.0 percent. Lubricants according to the present invention may be used in the amount of up to 20 weight percent, and preferably between 0.5 and about 4 weight percent based on the total composition.

Most preferably, the solid dosage forms in accordance with the present invention also include at least one effervescent disintegration agent. The term "effervescent disintegration agent" includes compounds which evolve gas. The preferred effervescent agents evolve gas by means of a chemical reaction which takes place upon exposure of the effervescent disintegration agent to water and/or to saliva in the mouth. This reaction is most often the result of the reaction of a soluble acid source and an alkali monocarbonate or carbonate source. The reaction of these two general compounds produces carbon dioxide gas upon contact with water or saliva. Such water-activated materials must be kept in a generally anhydrous state and with little or no adsorbed moisture or in a stable hydrated form, since exposure to water will prematurely disintegrate the tablet. The acid sources may be any which are safe for human consumption and may generally include food acids, acid and hydrite antacids such as, for example, citric, tartaric, amalic, fumeric, adipic, and succinics. Carbonate sources include dry solid carbonate and bicarbonate salt such as, preferably, sodium bicarbonate, sodium carbonate, potassium bicarbonate and potassium bicarbonate, magnesium carbonate and the like. Reactants which evolve oxygen or other gases and which are safe for human consumption are also included. In general, the amount of effervescent disintegration agent used in accordance with the present invention should range from between about 1 percent to 50 percent by weight of the final composition and preferably between 3 percent and about 30 percent by weight thereof. In a more preferred embodiment, the amount of effervescence disintegration agent according to the present invention ranges from between about 5 percent and about 25 percent by weight of the solid dosage form.

In the case of the orally disintegratable tablets in accordance with the present invention, it is preferred that the amount of disintegration agent, either effervescent or noneffervescent or the combination thereof provided be sufficient such that the tablet provides a pleasant organoleptic sensation in the mouth of the patient. In some instances, the patient should be able to perceive a distinct sensation of fizzing or bubbling as the tablet disintegrates in the mouth. In general, the amount of either effervescence disintegration agent, noneffervescence disintegration agent or both in accordance with the present invention should be sufficient to allow for disintegration to offer the rapid and complete disintegration of the tablet when orally administered. By rapid, it is understood that the tablets of the present invention should disintegrate in the mouth of the patient in less than 10 ten minutes and desirably less than 1 minute. Most preferably, the tablet will dissolve as quickly as possible, in as little as a few seconds. Disintegration time in the mouth can be measured by observing the disintegration time of the tablet in water about 37° C. The tablet is immersed in the water without forcible agitation or with minimal agitation. The disintegration time is the time from immersion for substantially complete dispersion of the tablet as determined by visual observation. Complete disintegration of the tablet does not require dissolution or disintegration of the microparticles or other discrete materials included.

Dosage forms in accordance with the present invention can be made in a number of ways. Particularly advantageous dosage forms in accordance with the present invention, will rapidly dissolve in the mouth and incorporate at least some amount of effervescence. Therefore, in accordance with the present invention, dosage forms can be produced generally by the teachings of Wehling et al., U.S. Pat. No. 5,178,878 the complete text of which is hereby incorporated by reference.

Any other conventional method of tableting can also be used in accordance with the present invention. It is preferable that the pressure used to tablet the dosage forms of the present invention be relatively small when rapid disintegratable effervescent tablets, for example, are produced. The lower compression used will aid in rapid disintegration. Lower compression should also be used when fragile or rupturable microparticles are used.

The rupturability of a microparticle can be measured on a practical basis, by subjecting the microparticles to a chewing test. If the taste of the pharmaceutical ingredient can be observed by a normal observer after chewing a reasonable portion of such microparticle, such as approximately 250 milligrams thereof, for about 30 seconds, then the microparticles can be considered susceptible to release of the pharmaceutical ingredient upon rupture. An alternative test may be performed by subjecting the microparticles to the physical forces encountered in a tableting press and determining whether or not the propensity of the microparticles to release the pharmaceutical ingredient has increased. One practical test using that approach is to make a tableting mixture using the following ingredients:

TABLE A

| Ingredient | Mg/Tablet |
| --- | --- |
| Mannitol | 225.0 mg |
| Magnesium Stearate | 5.0 mg |
| Silicon Dioxide | 1.0 mg |
| Microparticles | 90–100 mg |

That tableting mixture is then tableted in a conventional tableting press to a relatively low hardness value, preferably about 1.5 kilo pounds and, separately, to a higher hardness value of about 4 kilo pounds. These tablets are then compared to determine whether the harder tablet has a greater propensity to release the pharmaceutical ingredient. Where the pharmaceutical ingredient has a significant taste, the comparison can be made by placing the tablets on the tongue in separate trials and allowing the tablet to dissolve without chewing. If the harder tablet (4 kilo pounds) provides a stronger taste, then the microparticles can be considered susceptible to rupture.

Where, however, a chewable tablet is produced, and where more durable microparticles are utilized, compression may be more severe. In general, tablets will be formed using a pressure such that their hardness ranges from between about 5 to about 250 and more preferably between about 10 to about 50 [newtons]. Tablets can be produced in accordance with any known methods such as those described in *Pharmaceutical Dosage Form: Tablets, Volume* 1, Second Edition, Herbert A. Lieberman.

The foregoing will be better understood with reference to the following examples which detail certain procedures for manufacture of tablets in accordance to the present invention. All references made to these examples are for the purposes of illustration. They are not to be considered limiting as to the scope and nature of the present invention.

EXAMPLE I

Chlorpheniramine maleate (CM)

CM has a very bitter taste and a very unpleasant aftertaste. CM was granulated with mannitol and then coated. Specifically, several 5.0 percent CM granulations were prepared using a Zanchetta 50 liter vertical high shear granulator/processor. The formulation is shown in Table 1.

TABLE 1

| Material | Quantity (mg/gm) |
| --- | --- |
| Chlorpheniramine maleate USP | 50.0 |
| Mannitol powder USP | 930.0 |
| Polyvinylpyrrolidone K-30 USP | 20.0 |
| Total | 1,000.0 |

The granulation was produced using the following procedure:

Polyvinylpyrrolidone K-30 USP (240.0 gm) was dissolved into distilled water (1,890.0 gm) with agitation. Mannitol powder USP (11,160 gm) and chlorpheniramine maleate USP (600.0 gm) were placed in the Zanchetta 50-liter granulator/processor. After an initial two-minute dry mix of the powders with the chopper on and the propeller adjusted to 200 rpm, the polyvinylpyrrolidone K-30 solution was slowly sprayed into the mixing powder bed using an air-driven spray system. The total time of granulation including the time of solution addition was eight minutes. The granulation end-point was determined visually and by the consistency of the resulting material. The material was then discharged onto trays and dried at 80° C. utilizing supplied dry air for a period of six hours to a moisture content of not more than 0.08 percent. The dried material was then passed through a hammermill (knives forward) equipped with a U.S. #40 (420 micron) screen. The milled material was then screened through a U.S. #200 (75 micron) screen. The material retained on the U.S. #200 (75 micron) screen, about 50 percent, had a mean particle size of 210 microns and was retained for overcoating.

EXAMPLE II

COATING

Several batches of the 5.0 percent CM granulation produced in accordance with Example I were overcoated to a 15 percent coating level weight based on weight of finished granule using a 5-liter fluidized bed spray coating unit. The formulation for the overcoated CM (4.25 percent w/w) is shown in Table 2.

TABLE 2

Formulation for overcoated chlorpheniramine maleate (4.25 w/w)

| Material | Quantity (mg/gm) | Label Claim (mg/gm) |
| --- | --- | --- |
| Chlorpheniramine maleate granulation (5.0% w/w) | 850.0 | 42.5 |
| Ethylcellulose NF | 82.5 | |
| Polyvinylpyrrolidone K-30 USP | 60.0 | |
| Distilled Acetylated Monoglycerides | 7.5 | |
| Total | 1,000.0 | |

The coated particles of CM material were produced as follows: The coating solution consisted of polyvinylpyrrolidone K-30 USP (360 gm), ethylcellulose NF (495 gm), and distilled acetylated monoglycerides (45 gm). These solids were dissolved in a mixture of SD3A denatured alcohol (1,350 gm) and acetone NF (6,750 gm) with agitation. Five kilograms of chlorpheniramine maleate granulation (5.0% w/w) was placed into the 5-liter chamber of the fluidized bed coating unit. The bed was fluidized with air heated to 38° C. and the coating solution was sprayed into the fluidized powder bed using atomized spray at a rate of approximately 50 gm/min. until a 15 percent w/w (solids) coating level was reached. After the endpoint was reached, the material was allowed to dry in the fluidized bed for an additional ten minutes to drive off any residual solvents. The mean particle size of the overcoated material was 307 microns. The particle size distribution for overcoated chlorpheniramine is shown in FIG. 3. The resulting material was evaluated for taste and little aftertaste was detected by taste testing. Dissolution testing was performed on the coated material in 500 ml of water at 37° C. using the USP paddle method at 200 rpm. The results of the dissolution testing conducted on the overcoated chlorpheniramine maleate granulation are shown in Table 3.

TABLE 3

Dissolution of overcoated chlorpheniramine maleate granulation Lot #940308-A1

| Time (min) | % Dissolved (average of 3 cells) | RSD (%) |
| --- | --- | --- |
| 10 | 98.2 | 0.41 |
| 20 | 99.8 | 0.26 |
| 30 | 99.2 | 0.40 |
| 40 | 98.8 | 0.55 |
| 50 | 98.8 | 0.45 |

EXAMPLE III

Dextromethorphan HBr (DEX)

Several 20.0 percent DEX granulations were also prepared for polymer overcoating using a Zanchetta 50 liter vertical high shear granulator/processor. DEX, like CM, has a very bad bitter taste and a bad after taste. The following DEX formulations were granulated:

TABLE 4

Formulation for 20.0%
dextromethorphan HBr granulation

| Material | Quantity (mg/gm) |
| --- | --- |
| Dextromethorphan HBr USP | 200.0 |
| Mannitol powder USP | 750.0 |
| Polyvinylpyrrolidone K-30 USP | 50.0 |
| Total | 1,000.0 |

The granulation was produced using the following procedure: Polyvinylpyrrolidone K-30 USP (600.0 gm) was dissolved into distilled water (1,500.0 gm) with agitation. Mannitol powder USP (9,000.0) gm) and dextromethorphan HBr USP (2,400.0 gm) were placed in a Zanchetta 50-liter granulator/processor. After an initial two-minute dry mix of the powders with the chopper on and the propeller adjusted to 200 rpm, the polyvinylpyrrolidone K-30 solution was slowly sprayed into the mixing powder bed using an air-driven spray system. The total time of granulation including the time of solution addition was eleven minutes. The granulation end-point was determined visually and by the consistency of the resulting material. The material was then discharged onto trays and dried at 80° C utilizing supplied dry air for a period of six hours to a moisture content of not more than 0.08 percent. The dried material was then passed through a hammermill (knives forward) equipped with a U.S. #40 (420 micron) screen. The milled material was then screened through a U.S. #200 (75 micron) screen. The material retained on the U.S. #200 (75 micron) screen, about 60 percent, had a mean particle size of 213 microns and was retained for overcoating.

EXAMPLE IV

COATING

Several batches of the 20% dextromethorphan HBr granulation were overcoated to a 50% coating level using a liter fluidized bed spray coating unit. The formulation for the overcoated dextromethorphan HBr (10.0% ww) is shown in Table 5.

TABLE 5

Formulation for overcoated
dextromethorphan HBr (10.0% w/w)

| Material | Quantity (mg/gm) | Label Claim (mg/gm) |
| --- | --- | --- |
| Dextromethorphan HBr granulation (20.0% w/w) | 500.0 | 100.0 |
| Ethylcellulose NF | 275.0 | |
| Polyvinylpyrrolidone K-30 USP | 200.0 | |
| Distilled Acetylated Monoglycerides | 25.0 | |
| Total | 1,000.0 | |

The coating solution consisted of polyvinylpyrrolidone K-30 USP (1,200 gm), ethylcellulose NF (1,650 gm), and distilled acetylated monoglycerides (150 gm). These solids were dissolved in a mixture of SD3A denatured alcohol (4,500 gm) and acetone NF (22,500 gm) with agitation. Three kilograms of dextromethorphan Hbr granulation (20.0% w/w) were placed into the 5-liter chamber of the fluidized bed coating unit. The bed was fluidized with air heated to 38° C. and the coating solution was sprayed into the fluidized powder bed using an atomized spray at a rate of approximately 50 gm/min. until a 50 percent w/w (solids) coating level was reached. After the end-point was reached, the material was allowed to dry in the fluidized bed for an additional ten minutes to drive off any residual solvents. The mean particle size of the overcoated material was 379 microns. The resulting material was evaluated for taste as described in Example 2 and little or no aftertaste was detected. Dissolution testing was performed on the coated material in 500 ml of 0.1N HCl at 37° C. using the USP paddle method at 200 rpm. The results of the dissolution testing conducted on the overcoated dextromethorphan granulation are shown in Table 6.

TABLE 6

Dissolution of overcoated
dextromethorphan HBr granulation
Lot #940303-A1

| Time (min) | % Dissolved (average of 3 cells) | RSD (%) |
| --- | --- | --- |
| 10 | 92.1 | 0.56 |
| 20 | 94.2 | 0.46 |
| 30 | 94.8 | 0.23 |
| 40 | 95.2 | 0.23 |
| 50 | 94.7 | 0.36 |

EXAMPLE V

PEDIATRIC COUGH/COLD TABLETS

Pediatric cough/cold tablets were manufactured utilizing active ingredients which have been microencapsulated in accordance with the present invention along with another off-the-shelf encapsulated active (pseudoephedrine HCl). A typical formulation of a three drug cough/cold product is shown in Table 7. The tablets were evaluated by a taste panel for drug aftertaste. The consensus of the taste panel on these tablets was that there was no detectable drug aftertaste.

TABLE 7

Typical formulation for OraSolv
cough/cold tablets

| Material | Quantity mg/tab |
| --- | --- |
| Encapsulated Pseudoephedrine HCl (67.9% w/w) | 22.10 |
| Coated Chlorpheniramine Maleate Granulation (4.25% w/w) | 23.50 |
| Coated Dextromethorphan HBr Granulation (10.0% w/w) | 50.00 |
| Mannitol powder USP | 396.00 |
| Sodium Bicarbonate USP | 32.00 |
| Citric Acid USP | 23.00 |
| Aspartame NF | 35.00 |
| Potassium Carbonate USP | 8.00 |
| Prosweet Powder | 8.00 |
| Silicon Dioxide USP | 1.30 |
| Bubble Gum Flavors | 10.00 |
| Sodium Chloride USP | .80 |
| Pink Lake Blend | 2.40 |
| Magnesium Stearate NF | 10.00 |
| Total | 622.10 |

EXAMPLE VI

GRANULATION OF CHLORPHENIRAMINE MALEATE (CM)

Sufficient granulating solution to manufacture eight granulated batches (190.00 Kg) was prepared in a single tank. The solids were slowly added to the liquid with agitation. The mixture was agitated using an air mixer equipped with a paddle until all of the solids were completely dissolved. Each raw material, the corresponding lot number and manufacturer, and the quantity used in manufacturing the granulating solution is outlined in Table 8. The granulating solution was composed of approximately 21.1% solids.

TABLE 8

| Granulating Solution Raw Materials | | | |
|---|---|---|---|
| Raw Material | Lot Number | Manufacturer | Quantity (Kg) |
| Chlorpheniramine Maleate, USP | 43010S | Napp | 20.00 |
| Hysol SDA 3AP = 200 Ethanol | 0419941CGE-SDA | Hudrite | 15.00 |
| Povidone C-30, USP | TX30714 | ISP | 8.00 |
| Mannitol, USP | ESLY2 | Roquette | 12.00 |
| Distilled Water, USP | 12-02-93 | Hinckley & Schmitt | 135.00 |

Mannitol comprises 100% of the material that is initially charged into the fluidized bed for the granulation process. As received from the vendor, the mannitol has a tendency to compact and form agglomerates during shipment. To eliminate these agglomerates, a deagglomeration procedure was implemented. The deagglomeration process involves passing the mannitol through a Frewitt® oscillating granulator equipped with a US No. 20 screen. Sufficient mannitol was deagglomerated to generate eight batches of granulated material. Table 2 shows the lot number(s) of mannitol used and the corresponding lot number of the manufactured granulations.

TABLE 9

| Mannitol Lot Number(s) | | |
|---|---|---|
| Granulation Lot Number | Quantity (Kg) | Mannitol Lot Number |
| 940711-L1 | 45.00 | E3LY2 |
| 940711-L2 | 45.00 | E3LY2 |
| 940711-L4 | 45.00 | E3LY2 |
| 940711-L5 | 45.00 | E3LY2 |
| 940711-L6 | 45.00 | E3LY2 |
| 940711-L7 | 16.30 | E3LY2 |
|  | 28.70 | E3FT4 |
| 940712-L1 | 45.00 | E3FT4 |

A total of eight granulations were attempted. The first run was aborted due to the inlet air temperature being set too low. This resulted in a low bed temperature and "overgranulation". The inlet temperature was increased before proceeding to the next batch. The last run was also aborted due to problems with the gear pump.

The 18" bottom spray fluidized bed "L" unit (Manufactured by the Coating Place) was charged with 45.00 Kg of deagglomerated mannitol. Using a gear pump and an air atomizing spray nozzle, 23.75 Kg of granulating solution were applied to the mannitol in the fluidized bed. Run parameters that were monitored during the runs include time, inlet temperature, outlet temperature, bed temperature, air flow, pump seed, atomizing air pressure, atomizing air volume, liquid line pressure, filter pressure, and the ambient conditions on startup. The amount of granulating solution applied was monitored on a scale. When the endpoint was reached, the pump was turned off and the lines were flushed for one minute. The inlet temperature was then increased and the granulation was directed to a bed temperature of 95° F. The granulation was passed through an ATM Sonic Sifter equipped with a US No. 30 screen. Oversized and undersized material were collected separately. The composition (theoretical) of the resulting granulation on a dry basis is shown in Table 10. The major run parameters for each run are reported in Table 11.

TABLE 10

| Composition (Theoretical) of Granulation on a Dry Basis | | |
|---|---|---|
| Raw Material | Kg | % w/w |
| Chlorpheniramine Maleate, USP | 2.50 | 5.0 |
| Mannitol, USP | 46.50 | 93.0 |
| Povidone C-30, USP | 1.00 | 2.00 |

[Note to the Inventors: Why are you only reporting theoretical values?]

TABLE 11

| Composition of Major Run Parameters and Results | | | | | | |
|---|---|---|---|---|---|---|
| Lot Number | Spray Rate | Inlet Temp. Actual (°F.) | Bed Temp. (°F.) | Ambient Temp (°F.) | Ambient Humidity (% R.H.) | Results |
| 940711-L1 | 350 | 110 | 76 | 78.1 | 66.7 | Aborted |
| 940711-L2 | 350 | 165 | 92 | 83.1 | 64.2 | Acceptable |
| 940711-L3 | 350 | 150 | 85 | 84.0 | 65.5 | Acceptable |
| 940711-L4 | 350 | 150 | 87 | 84.2 | 65.5 | Acceptable |
| 940711-L5 | 350 | 155 | 87 | 82.0 | 73.0 | Acceptable |

TABLE 11-continued

Composition of Major Run Parameters and Results

| Lot Number | Spray Rate | Inlet Temp. Actual (°F.) | Bed Temp. (°F.) | Ambient Temp (°F.) | Ambient Humidity (% R.H.) | Results |
|---|---|---|---|---|---|---|
| 940711-L6 | 350 | 155 | 88 | 77.0 | 81.0 | Acceptable |
| 940711-L7 | 350 | 155 | 87 | Omitted | Omitted | Acceptable |
| 940712-L1 | Pump Problems | N/A | N/A | Omitted | Omitted | Aborted |

The final step of the granulation process involved passing the granulation through an ATM Sonic Sifter equipped with a US No. 30 screen. Oversized and undersized material were collected separately. Only the material passing through the US No. 30 screen was used for coating. The oversized material was retained so that testing could be performed on the material at a later date. Table 12 shows the lot numbers and quantities of the granulations that were coated and the corresponding lot numbers assigned to the coated material.

TABLE 12

Granulations and Corresponding Lot Numbers of Coated Material

| Granulation Lot Number | Quantity (Kg) | Coated Lot Number |
|---|---|---|
| 940711-L4 | 40.00 | 940712-L1 |
| 940711-L2 | 35.00 | 940712-L2 |
| 940711-L3 | 35.00 | 940713-L1 |
| 940711-L5 | 35.00 | 940713-L2 |
| 940711-L6 | 35.00 | 940713-L3 |
| 940711-L7 | 35.00 | 940713-L4 |
| 940711-L3 | 8.19 | 940713-L6 |
| 940711-L5 | 12.52 | |
| 940711-L4 | 5.82 | |
| 940711-L2 | 8.47 | |

EXAMPLE VII

COATING THE CM

Four batches (90.00 Kg each), and one batch (85.00 Kg) of coating solution were manufactured as needed. The solids were slowly added to the liquids with agitation. The mixture was agitated using an air mixer equipped with a paddle until a homogeneous dispersion was obtained. Each raw material, the corresponding lot number and manufacturer, and the quantity used in manufacturing the 90 Kg batches of coating solution are outlined in Table 13. The same lot numbers of raw materials were used for all batches of coating solution. The coating solution is composed of 10.0% solids.

Six individual lots of granulation were coated to a 15% coating level. A seventh batch of coated material was produced utilizing a mixture of four of the granulations. This batch was also coated to a 15% coating level. Mixing of the granulations was performed to confirm that this procedure will result in acceptable product as mixing of lots will occur once the product is commercially produced.

For the first batch, the 18" bottom spray fluidized bed "L" unit (manufacturing by the Coating Place) was charged with 40.00 Kg of granulation. Using a gear pump and an air atomizing spray nozzle, 70.60 Kg of coating solution were applied to the granulation in the fluidized bed. For the second, and subsequent batches, the batch size was reduced to 35.00 Kg of granulation, with 61.75 Kg of coating solution being applied. The batch size was reduced because Coating Place personnel felt that we were exceeding the capacity of the chamber. Run parameters that were monitored during the runs include time, inlet temperature, outlet temperature, bed temperature, air flow, pump speed, atomizing air pressure, atomizing air volume, liquid line pressure, filter pressure, and the ambient conditions on startup. The amount of coating solution applied was monitored on a scale. When, the endpoint was reached, the pump was turned off and the lines were flushed for three minutes. The coated material was then dried for ten minutes to a bed temperature of approximately 90° F. The material was then passed through an 18" Sweco equipped with a US No. 20 screen. Oversized and undersized material were collected separately. The undersized material was considered usable and the oversized material unusable. The composition (theoretical) of the resulting coated material on a dry basis is shown in Table 14. The major run parameters for each run are reported in Table 15.

TABLE 13

Coating Solution Raw Materials

| Raw Material | Lot Number | Manufacturer | Quantity (Kg) |
|---|---|---|---|
| Ethocel Standard-10 Premium | MM931129-1 | Dow | 4.95 |
| Povidone C-30, USP | TX30714 | ISP | 3.60 |
| Myvacet 9-45K | D1817-0592 | Eastman Kodak | 0.45 |
| Hysol SDA 3AP-200 Ethanol | 0419941CGE-SDA | Hydrite | 13.50 |
| Acetone, NF | 0419941CGE-ACE | Hydrite | 67.50 |

TABLE 14

Composition (Theoretical) of Coated Material on a Dry Basis

| Raw Material | Kg | % w/w |
|---|---|---|
| Chlorpheniramine Maleate, USP | 1.77 | 4.25 |
| Myvacet 9-45K | 0.31 | 0.75 |
| Ethocel Standard-10 Premium | 3.44 | 8.25 |
| Mannitol, USP | 33.00 | 79.05 |
| Povidone C-30, USP | 3.21 | 7.70 |

TABLE 15

Composition of Major Run Parameters and Results

| Lot Number | Spray Rate | Inlet Temp. Actual (°F.) | Bed Temp. (°F.) | Ambient Temp (°F.) | Ambient Humidity (% R.H.) | Results |
|---|---|---|---|---|---|---|
| 940712-L1 | 370–450 | 110 | 80–90 | Omitted | Omitted | Acceptable |
| 940712-L2 | 445 | 110 | 80 | Omitted | Omitted | Acceptable |
| 940713-L1 | 450 | 110 | 76 | Omitted | Omitted | Acceptable |
| 940713-L2 | 465–495 | 108 | 73 | Omitted | Omitted | Acceptable |
| 940713-L3 | 520 | 110 | 75 | Omitted | Omitted | Acceptable |
| 940713-L4 | 525 | 110 | 75 | Omitted | Omitted | Acceptable |
| 940713-L6 | 525 | 110 | 75 | Omitted | Omitted | Acceptable |

EXAMPLE VIII

CM COATED GRANULE TABLE FORMATION

One-tenth scale definitive stability batches of the bubble gum and grape flavored two and three drug tablets were produced with material manufactured in the previous EXAMPLES VI and VII. The tablets were ½" in diameter with a target weight of 625 mg. Tablets were flat faced with a beveled edge. Target hardness was 10–15 newtons. The three drug tablets contained 88.5 mg. of encapsulated active and the two drug tablets contained 48.5 mg. of encapsulated active. In all cases, taste and overall produce quality was acceptable.

EXAMPLE IX

GRANULATION OF DEXTROMETHORPHAN Hbr (DEX)

Sufficient granulating solution (180.00 Kg) was prepared in a single tank to manufacture eight granulated batches. The solids were slowly added to the liquid with agitation. The mixture was agitated using an air mixer equipped with a paddle until all of the solids were completely dissolved. Each raw material, the corresponding lot number and manufacturer, and the quantity used in manufacturing the granulating solution is outlined in Table 16. The granulating solution is composed of 20.0% solids.

TABLE 16

Granulating Solution Raw Materials

| Raw Material | Lot Number | Manufacturer | Quantity (Kg) |
|---|---|---|---|
| Povidone C-30, USP | TX30714 | ISP | 14.40 |
| Mannitol, USP | E3FT4 | Roquette | 21.60 |
| Distilled Water, USP | 12-02-93 | Hinckley & Schmitt | 144.00 |

As received from the vendor, the Dextromethorphan Hbr has a tendency to form agglomerates during shipment. Since the DEX is not dissolved into the granulating solution, but placed directly into the fluidized bed, a deagglomeration procedure was implemented to assure uniform fluidization of the active during granulation. The deagglomeration process involves passing the DEX through a Frewitt® oscillating granulator equipped with a US No. 20 screen. Sufficient DEX was deagglomerated to generate eight batches of granulated material.

Mannitol comprises approximately 77% of the material that is initially charged into the fluidized bed for the granulation process. As received from the vendor, the mannitol also has a tendency to compact and form agglomerates during shipment. To eliminate these agglomerates, a deagglomeration procedure was implemented. The deagglomeration process involves passing the mannitol through a Freewitt® oscillating granulator equipped with a US No. 20 screen. Sufficient mannitol was deagglomerated to generate eight batches of granulated material. Table 17 shows the lot number(s), quantities, and manufacturer of the mannitol and DEX used, and the corresponding lot number of the manufactured granulations.

TABLE 17

Mannitol and Dextromethorphan Hbr Lot Numbers

| Granulation Lot Number | Lot Number | Mannitol Quantity | Manufacturer | Dextromethorphan HBr Lot Number | Quantity | Manufacturer |
| --- | --- | --- | --- | --- | --- | --- |
| 940815-L1 | E3FT4 | 31.50 Kg | Roquette | 312860 | 9.45 Kg | Roche |
| 940815-L2 | E3FT4 | 31.50 Kg | Roquette | 403920 | 9.45 Kg | Roche |
| 940815-L3 | E3FT4 | 31.50 Kg | Roquette | 403920 | 9.45 Kg | Roche |
| 940815-L4 | E3FT4 | 31.50 Kg | Roquette | 403920 | 9.45 Kg | Roche |
| 940815-L5 | E3FT4 | 31.50 Kg | Roquette | 403920 | 9.45 Kg | Roche |
| 940816-L1 | E3FT4 | 31.50 Kg | Roquette | 403920 | 9.45 Kg | Roche |
| 940816-L2 | E3FT4 | 31.50 Kg | Roquette | 403920 | 9.45 Kg | Roche |

A total of seven granulations were manufactured. The 18" bottom spray fluidized bed "L" unit (manufactured by the Coating Place) was charged with 31.50 Kg of deagglomerated mannitol and 9.45 Kg of deagglomerated DEX. An overage of 0.45 Kg of DEX was added to compensate for the 4.5% water contained in the raw material. Using a gear pump and an air atomizing spray nozzle, 22.50 Kg of granulating solution were applied to the mannitol and drug in the fluidized bed. Run parameters that were monitored during the runs include time, inlet temperature, outlet temperature, bed temperature, air flow, pump speed, atomizing air pressure, atomizing air volume, liquid line pressure, filter pressure, and the ambient conditions on startup. The amount of granulating solution applied was monitored on a scale. When the endpoint was reached, the pump was turned off and the lines were flushed for one minute. The inlet temperature was then increased and the granulation was dried to a bed temperature of 100° F. The granulation was passed through an 18" Sweco equipped with a TBC 34 mesh screen. Oversized and undersized material were collected separately. The composition (theoretical) of the resulting granulation on a dry basis is shown in Table 18. The major parameters for each batch are reported in Table 19.

TABLE 18

Composition (Theoretical) of Granulation on a Dry Basis

| Raw Material | Kg | % w/w |
| --- | --- | --- |
| Dextromethorplan Hbr, USP | 2.50 | 20.0 |
| Mannitol, USP | 46.50 | 76.0 |
| Povidone C-30, USP | 1.00 | 4.0 |

TABLE 19

Composition of Major Run Parameters and Results

| Lot Number | Spray Rate (g/min) | Inlet Temp. Actual (°F.) | Bed Temp. (°F.) | Ambient Temp (°F.) | Ambient Humidity (% R.H.) | Results |
| --- | --- | --- | --- | --- | --- | --- |
| 940815-L1 | 350 | 150–165 | 80–88 | 73.1 | 49.8 | Acceptable |
| 940815-L2 | 350 | 148–160 | 84–94 | 78.1 | 42.9 | Acceptable |
| 940B15-L3 | 350 | 155–160 | 87–90 | 74.0 | 53.0 | Acceptable |
| 940815-L4 | 350 | 160 | 87–88 | 67.0 | 74.4 | Acceptable |
| 940815-L5 | 350 | 160 | 87 | 62.0 | 85.5 | Acceptable |
| 940816-L1 | 350 | 160 | 88 | 60.0 | 81.0 | Acceptable |
| 940816-L2 | 350 | 160 | 88 | 59.1 | 76.8 | Acceptable |

The final step of the granulation process involved passing the granulation through an 18" Sweco equipped with a TBC No. 34 mesh screen. Oversized and undersized material were collected separately. Only the material passing through the TBC No. 34 mesh screen was used for coating. The oversized material was retained so that testing could be performed on the material at a later date. Table 20 shows the lot numbers and quantities of the granulations that were coated and the corresponding lot numbers assigned to the coated material.

TABLE 20

Granulations and Corresponding Lot Numbers of Coated Material

| Granulation Lot Number | Quantity (Kg) | Coated Lot Number |
| --- | --- | --- |
| 940815-L1 | 26.00 | 940816-L3 |
| 940815-L2 | 26.00 | 940816-L4 |
| 940815-L3 | 26.00 | 940817-L1 |
| 940815-L4 | 26.00 | 940817-L2 |
| 940815-L5 | 26.00 | 940818-L1 |
| 940815-L5 | 16.29 | 940818-L2 |
| 940816-L1 | 9.71 | |
| 940816-L1 | 13.00 | 940818-L3 |
| 940816-L2 | 13.00 | |
| 940816-L1 | 13.00 | 940819-L1 |
| 940816-L2 | 13.00 | |

EXAMPLE X

COATING THE DEX GRANULES

Seven batches (145.00 Kg each) of coating solution were manufactured. The solids were slowly added to the liquids with agitation. The mixture was agitated using an air mixer equipped with a paddle until a homogeneous dispersion was obtained. Each raw material, the corresponding lot number and manufacturer, and the quantity used in manufacturing the coating solutions are outlined in Table 21. The coating solution is composed of 10.0% solids.

Five individual lots of granulation were coated to a 35% coating level. Three additional batches of coated material were produced utilizing a mixture of two granulations. These batches were also coated to a 35% coating level mixing of the granulations was performed to confirm that this procedure will result in acceptable product as mixing of lots will occur once the product is commercially produced.

For all batches, the 18" bottom spray fluidized bed "L" unit (manufactured by the Coating Place) was charged with 26.00 Kg of granulation. Using a gear pump and an air atomizing spray nozzle, 140.00 Kg of coating solution were applied to the granulation in the fluidized bed. Run parameters that were monitored during the runs include time, inlet temperature, outlet temperature, bed temperature, air flow, pump speed, atomizing air pressure, atomizing air volume, liquid line pressure, filter pressure, and the ambient conditions on startup. The amount of coating solution applied was monitored on a scale. When the endpoint was reached, the pump was turned off and the lines were flushed for three minutes. The inlet temperature was then increased to 150° F. and the product was dried to a bed temperature of approximately 95° F. The material was then passed through an 18" Sweco equipped with a US No. 20 screen. Oversized and undersized material were collected separately. The undersized material was considered usable and the oversized material unusable. The composition (theoretical) of the resulting coated material on a dry basis is shown in Table 22. The major run parameters for each run are reported in Table 23.

TABLE 21

Coating Solution Raw Materials

| Coating Solution Lot Number | Raw Material | | Lot Number | Manufacturer | Quantity (Kg) |
|---|---|---|---|---|---|
| CS400B-COAT-1 | Ethocel Premium | Standard-10 | MM931129-1 | Dow | 2.49 |
| | Ethocel Premium | Standard-10 | MM940103-1 | Dow | 6.21 |
| | Povidone C-30, USP | | TX30714 | ISP | 4.35 |
| | Myvacet 9-45K | | D1813-0592 Kodak | Eastman | 1.45 |
| | Hysol SDA Ethanol | 3AP-200 | 0419941CGE-SDA | Hydrite | 21.75 |
| | Acetone, NF | | 071594CGL-ACE | Hydrite | 108.75 |
| CS400B-COAT-2 | Ethocel Premium | Standard-10 | MM940103-1 | Dow | 8.70 |
| | Poidone C-30, USP | | TX30714 | ISP | 4.35 |
| | Myvacet 9-45K | | D1817-0592 Kodak | Eastman | 1.45 |
| | Hysol SDA Ethanol | 3AP-200 | 0419941CGE-SDA | Hydrite | 21.75 |
| | Acetone, NF | | 071594CGL-ACE | Hydrite | 108.75 |
| CS400B-COAT-3 | Ethocel Premium | Standard-10 | MM940103-1 | Dow | 8.70 |
| | Poidone C-30, USP | | TX30714 | ISP | 4.35 |
| | Myvacet 9-45K | | D1817-0592 Kodak | Eastman | 1.45 |
| | Hysol SDA Ethanol | 3AP-200 | 0419941CGE-SDA | Hydrite | 21.75 |
| | Acetone, NF | | 091594CGL-ACE | Hydrite | 108.75 |
| CS400B-COAT-4 | Same as CS400-COAT-3 | | | | |
| CS400B-COAT-5 | Same as CS400-COAT-3 | | | | |
| CS400B-COAT-6 | Ethocel Premium | Standard-10 | MM940103-1 | Dow | 8.70 |
| | Povidone C-30, USP | | TX40320 | ISP | 4.35 |
| | Myvacet 9-45K | | D1817-0592 Kodak | Eastman | 1.45 |
| | Hysol SDA Ethanol | 3AP-200 | 0419941CGE-SDA | Hydrite | 21.75 |
| | Acetone, NF | | 071594CGL-ACE | Hydrite | 65.15 |
| | Acetone, NF | | 0812941CGD-ACE | Hydrite | 43.60 |
| CS400-COAT-7 | Ethocel Premium | Standard-10 | MM940103-1 | Dow | 8.70 |
| | Povidone C-30, USP | | TX40320 | ISP | 4.35 |
| | Myvacet 9-45K | | D1817-0592 Kodak | Eastman | 1.45 |
| | Hysol SDA Ethanol | 3AP-200 | 0419941CGE-SDA | Hydrite | 21.75 |
| | Acetone, NF | | 0812941CGD-ACE | Hydrite | 108.75 |

TABLE 22

| Composition (Theoretical) of Coated Material on a Dry Basis | | |
| --- | --- | --- |
| Raw Material | Kg | % w/w |
| Dextromethorplan Hbr, USP | 5.20 | 13.00 |
| Myvacet 9-45K | 1.40 | 3.50 |
| Ethocel Standard-10 Premium | 8.40 | 21.00 |
| Mannitol, USP | 19.76 | 49.40 |
| Povidone C-30, USP | 5.24 | 13.10 |

TABLE 23

| | | Composition of Major Run Parameters and Results | | | | |
| --- | --- | --- | --- | --- | --- | --- |
| Lot Number | Spray Rate (g/min) | Inlet Temp. Actual (°F.) | Bed Temp. (°F.) | Ambient Temp (°F.) | Ambient Humidity (% R.H.) | Results |
| 940816-L3 | 395–550 | 110 | 77 | 81.0 | 43.1 | Aborted Spray Rate Too High |
| 940816-L4 | 250–400 | 110 | 75–84 | 70.0 | 75.0 | Acceptable |
| 940817-L1 | 250 | 110 | 83 | 83.1 | 51.7 | Acceptable |
| 940817-L2 | 250 | 110 | 83 | 71.0 | 77.0 | Acceptable |
| 940818-L1 | 250 | 110 | 84 | 67.0 | 100.0 | Acceptable |
| 940818-L2 | 250 | 110 | 86–89 | 71.3 | 94.4 | Acceptable |
| 940818-L3 | 250 | 113 | 88 | 67.5 | 94.0 | Acceptable |
| 940819-L1 | 320 | 122 | 90–95 | 78.0 | 72.4 | Acceptable |

These materials were incorporated into the three drug tablets described in Example VIII.

We claim:

1. A solid pharmaceutical dosage form adapted for direct oral administration, in solid form, to a mammal comprising:
a plurality of microparticles, each said microparticle having a core including at least one pharmaceutical ingredient and a compound which is sweet in taste and which has a negative heat of solution, said compound which is sweet in taste and which has a negative heat of solution being selected from the group consisting of mannitol, sorbitol, a mixture of an artificial sweetener and menthol, a mixture of a sugar and menthol, and methyl salicylate, said compound being present in said microparticles in an amount of between greater than 0 and about 80% by weight of the resulting microparticle, said core being coated with a coating material, which will retard dissolution of said pharmaceutical ingredient in the mouth, as well as the objectionable taste of said pharmaceutical ingredient, surrounding at least a portion of said core; said solid dosage form being sized and shaped and having a composition and hardness which are adapted for direct oral administration, said dosage form being disintegratable in the mouth so as to release said microparticles.

2. The dosage form of claim 1 further comprising at least one saliva activated effervescent agent in an amount which is effective to provide disintegration of said dosage form in the mouth of a patient, without chewing, to thereby release said microparticles.

3. The pharmaceutical dosage form of claim 1 wherein said microparticles are discrete particulate at least partially coated with said coating material.

4. The pharmaceutical dosage form of claim 3 wherein said microparticles are coated with said coating material.

5. The pharmaceutical dosage form of claim 1 wherein said pharmaceutical ingredient is adsorbed on said compound which is sweet in taste and which has a negative heat of solution.

6. The pharmaceutical dosage form of claim 1 wherein said pharmaceutical ingredient is intimately mixed with said compound which is sweet in taste and which has a negative heat of solution.

7. The pharmaceutical dosage form of claim 1 wherein said microparticles comprise between about 1 and 80% of the dosage form by weight.

8. The pharmaceutical dosage form of claim 7 wherein said compound which is sweet in taste and which has a negative heat of solution is selected from a group consisting of mannitol and sorbitol.

9. The pharmaceutical dosage form of claim 1 further comprising at least one binder disposed within said core.

10. The pharmaceutical dosage form of claim 1 wherein said coating material is ethylcellulose.

11. The pharmaceutical dosage form of claim 1 wherein the balance of the weight of the dosage form is composed of one or more compounds of the group consisting of lubricants, fillers, disintegrants, binding agents, disintegration agents, sweeteners, flavors, colorants.

12. The pharmaceutical dosage form of claim 1 wherein said coating material is provided in an amount of at least about 5% by weight, based on the weight of the particle.

13. The pharmaceutical dosage form of claim 12 wherein said coating material is provided in an amount of at least about 10% by weight, based on the weight of the particle.

14. The pharmaceutical dosage form of claim 12 wherein said coating material is provided in an amount at between about 5% and about 75% by weight of the microparticles.

15. The pharmaceutical dosage form of claim 1 wherein said dosage form is a tablet having a hardness ranging from between about 5 to about 250 newtons.

16. The tablet of claim 15 having a hardness of between about 10 and about 50 newtons.

17. The pharmaceutical dosage form of claim 7 wherein said microparticles comprise between about 5 and about 50% of the dosage form by weight.

* * * * *

UNITED STATES PATENT AND TRADEMARK OFFICE
CERTIFICATE OF CORRECTION

PATENT NO. : 5,607,697

DATED : March 4, 1997

INVENTOR(S) : Alkire et al.

Page 1 of 3

It is certified that error appears in the above-indentified patent and that said Letters Patent is hereby corrected as shown below:

```
Column 3, line 44, delete "have" and insert therefor --has--.
Column 5, line 3, delete "includes" and insert therefor
  --including--.
          line 8, "include" should read --includes--.
          line 41, after "to" insert --,--; after "example"
  insert --,--.
Column 6, line 2, after "however" insert --,--.
          line 39, after "amount" insert --of--.
          line 44, after "agglomeration," insert --or--; delete
             "may be used".
          line 48, delete "such binders may also be used".
Column 7, line 30, "impede" should read --impedes--.
Column 8, line 16, delete "Lieherman" and insert therefor
  --Lieberman--.
Column 9, line 43, delete "potassium bicarbonate".
Column 11, line 65, "spray coating" should read --spraycoating--
Column 13, line 43, before "liter" insert --5--.
Column 16, line 53 (after Table 10), delete "[Note to the
  Inventors:  Why are you only reporting theoretical values?]".
Column 19, in TABLE 15, under Bed Temp. (°F), line 4, delete "73"
  and insert therefor --77--.
          line 32, delete "20".
Column 21, in TABLE 17 (under the second occurrence of Lot
  Number), line 1, delete "312860" and insert therefor
  --312880--.
          in TABLE 19 (under Lot Number), line 3, delete
  "940B15-L3" and insert therefor --940815-L3--.
Column 23, line 8, after "level" insert --.--.
          line 9, "mixing" should read --Mixing--.
```

UNITED STATES PATENT AND TRADEMARK OFFICE
CERTIFICATE OF CORRECTION

PATENT NO. : 5,607,697
DATED : March 4, 1997
INVENTOR(S) : Alkire et al.

Page 2 of 3

It is certified that error appears in the above-indentified patent and that said Letters Patent is hereby corrected as shown below:

Columns 23 and 24, delete TABLE 21 and insert therefor

--TABLE 21

Coating Solution Raw Materials

| Coating Solution Lot Number | Raw Material | Lot Number | Manufacturer | Quantity (Kg) |
|---|---|---|---|---|
| CS400B-COAT-1 | Ethocel Standard-10 Premium | MM931129-1 | Dow | 2.49 |
| | Ethocel Standard-10 Premium | MM940103-1 | Dow | 6.21 |
| | Povidone C-30, USP | TX30714 | ISP | 4.35 |
| | Myvacet 9-45K | D1817-0592 | Eastman Kodak | 1.45 |
| | Hysol SDA 3AP-200 Ethanol | 0419941CGE-SDA | Hydrite | 21.75 |
| | Acetone, NF | 071594CGL-ACE | Hydrite | 108.75 |
| CS400B-COAT-2 | Ethocel Standard-10 Premium | MM940103-1 | Dow | 8.70 |
| | Poidone C-30, USP | TX30714 | ISP | 4.35 |
| | Myvacet 9-45K | D1817-0592 | Eastman Kodak | 1.45 |
| | Hysol SDA 3AP-200 Ethanol | 0419941CGE-SDA | Hydrite | 21.75 |
| | Acetone, NF | 071594CGL-ACE | Hydrite | 108.75 |
| CS400B-COAT-3 | Ethocel Standard-10 Premium | MM940103-1 | Dow | 8.70 |
| | Poidone C-30, USP | TX30714 | ISP | 4.35 |
| | Myvacet 9-45K | D1817-0592 | Eastman Kodak | 1.45 |
| | Hysol SDA 3AP-200 Ethanol | 0419941CGE-SDA | Hydrite | 21.75 |
| | Acetone, NF | 071594CGL-ACE | Hydrite | 108.75 |

UNITED STATES PATENT AND TRADEMARK OFFICE
CERTIFICATE OF CORRECTION

PATENT NO. : 5,607,697
DATED      : March 4, 1997
INVENTOR(S) : Alkire et al.

Page 3 of 3

It is certified that error appears in the above-indentified patent and that said Letters Patent is hereby corrected as shown below:

| | | | | |
|---|---|---|---|---|
| CS400B-COAT-4 | Same as CS400-COAT-3 | | | |
| CS400B-COAT-5 | Same as CS400-COAT-3 | | | |
| CS400-B-COAT-6 | Ethocel Standard-10 Premium | MM940103-1 | Dow | 8.70 |
| | Povidone C-30, USP | TX40320 | ISP | 4.35 |
| | Myvacet 9-45K | D1817-0592 | Eastman Kodak | 1.45 |
| | Hysol SDA 3AP-200 Ethanol | 0419941CGE-SDA | Hydrite | 21.75 |
| | Acetone, NF | 071594CGL-ACE | Hydrite | 65.15 |
| | Acetone, NF | 0812941CGD-ACE | Hydrite | 43.60 |
| CS400-COAT-7 | Ethocel Standard-10 Premium | MM940103-1 | Dow | 8.70 |
| | Povidone C-30, USP | TX40320 | ISP | 4.35 |
| | Myvacet 9-45K | D1817-0592 | Eastman Kodak | 1.45 |
| | Hysol SDA 3AP-200 Ethanol | 0419941CGE-SDA | Hydrite | 21.75 |
| | Acetone, NF | 0812941CGD-ACE | Hydrite | 108.75 |

--

Signed and Sealed this

Fifth Day of August, 1997

Attest:

BRUCE LEHMAN

*Attesting Officer*    *Commissioner of Patents and Trademarks*